April 11, 1972 B. L. COBIA Plant Pat. 3,105

HOYA CARNOSA RUBRA

Filed Feb. 16, 1970

INVENTOR
BARNELL L. COBIA
BY Roger L. Martin

United States Patent Office

Plant Pat. 3,105
Patented Apr. 11, 1972

3,105
*HOYA CARNOSA* RUBRA

Barnell L. Cobia, Winter Garden, Fla., assignor to
B. L. Cobia, Inc., Winter Garden, Fla.

Filed Feb. 16, 1970, Ser. No. 11,926
Int. Cl. A01h *5/00*
U.S. Cl. Plt.—88 1 Claim

ABSTRACT OF THE DISCLOSURE

A new and distinct plant variety of the milkweed family resembles plants of the *Hoya carnosa* Exotica variety in variegated leaf patterns but is distinguished from the latter variety by certain color characteristics, by slightly larger stems and by a somewhat wider leaf blade that is usually ovate in shape.

The invention relates to a new and distinct plant variety of the milkweed (Asclepiadaceae) family and which has been named the *Hoya carnosa* (CV) Rubra by the inventor.

Certain plants of the milkweed family are well known in the foliage plant market and among these are those of the *Hoya carnosa* Exotica variety and of the *Hoya carnosa* Variegata variety. A lesser known related variety found in the foliage plant market but which is rapidly gaining popularity is the *Hoya carnosa* Tricolor variety.

Plants of the *Hoya carnosa* Tricolor variety have variegated leaf blades which are similar in pattern to those of the *Hoya carnosa* Variegated variety but are preferred by comparing purchaser's in the market place because of certain characteristic colors which, in immature and newly matured growth, appear in the albino or variegated areas of the leaf blades.

Plants of the *Hoya carnosa* Exotica variety have variegated leaf blades but in contrast to the albino leaf blade border areas of the *Hoya carnosa* Variegated plant variety are characterized by an albino center field in the leaf blade. The main object of the invention has been to develop a plant variety which is related in general appearance to the *Hoya carnosa* Exotica plant variety but which exhibits colors in the albino leaf blade areas that are similar to those found in the *Hoya carnosa* Tricolor variety. The object of the invention has been fully realized as will be evident from the following detailed disclosure.

Plants of the new variety generally resemble plants of the *Hoya carnosa* Exotica variety and are not only related to this variety but also related to the *Hoya carnosa* Variegata and *Hoya carnosa* Tricolor varieties. The new variety is mainly distinguished from its antecedents and related varieties known to the inventor by a combination of certain color and structural characteristics which will be apparent subsequently. The new variety appeared as a sport on a plant of the *Hoya carnosa* Tricolor variety which was under cultivation in a nursery at Winter Garden, Fla., and since the initial discovery of the new variety, has been asexually reproduced by the inventor at the Winter Garden nursery by the propagation of stem cuttings taken from the original plant.

Through successive propagations, it has been ascertained that plants of the new variety generally resemble plants of the *Hoya carnosa* Exotica variety but are distinguishable from this plant variety and from other related varieties known to the inventor by a growth habit which combines the following characteristics:

(1) Larger diameter stems than those of the *Hoya carnosa* Exotica variety and which in color are dominated by purple, purplish red, red, reddish brown and/or pink hues prior to becoming glaucous;

(2) Leaves with petioles that in color are dominated by purple, purplish red, red, reddish brown, pink and/or yellowish pink hues prior to becoming glaucous, and with leaf blades that are somewhat broader than those of the *Hoya carnosa* Exotica variety, that are variegated in patterns characteristic of the *Hoya carnosa* Exotica variety, that have an albino center area which in color is dominated during early immaturity by purplish pink, purplish red, red and/or yellowish pink hues, and that have a green border area which is overcast during early immaturity with color endowing the border area to the ordinary eye with a blackish and/or brownish appearance; and (3) An inflorescence that has a peduncle color dominated by purplish red, red and/or reddish brown hues prior to becoming glaucous, a pedicel color dominated by purplish red and/or red hues, a sepal color dominated by purplish red, red and/or reddish brown hues, and a petal which in color at its upper epidermal side is dominated by purplish pink and/or pink hues and which in color at its lower epidermal side is dominated by a purplish red hue.

The accompanying drawings serve, by color photographic means, to illustrate the new variety and wherein.

Figure 1:
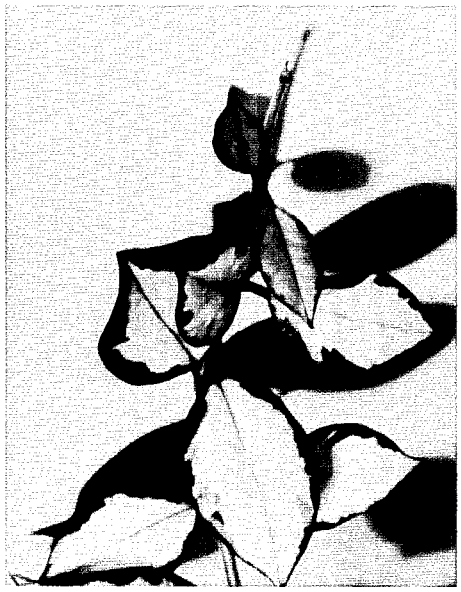
FIG. 1 is a color photograph of a plant specimen of the new variety and shows the upper epidermal sides of the leaves.
Figure 2:
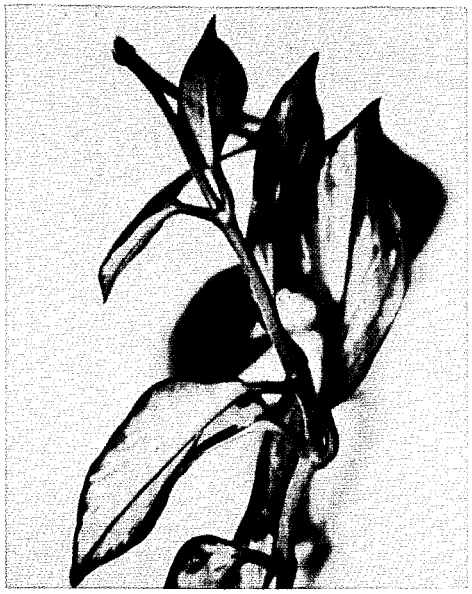
FIG. 2 is a color photograph of the specimen seen in FIG. 1 and shows the lower epidermal sides of the leaves.
Figure 3:
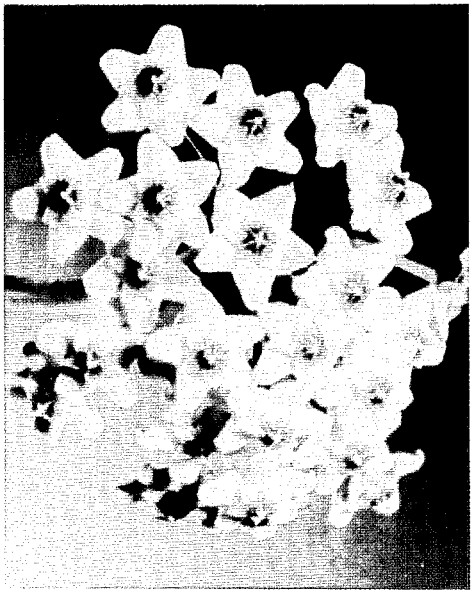
FIG. 3 is a color photograph of an inflorescence of the new variety.
Figure 4:
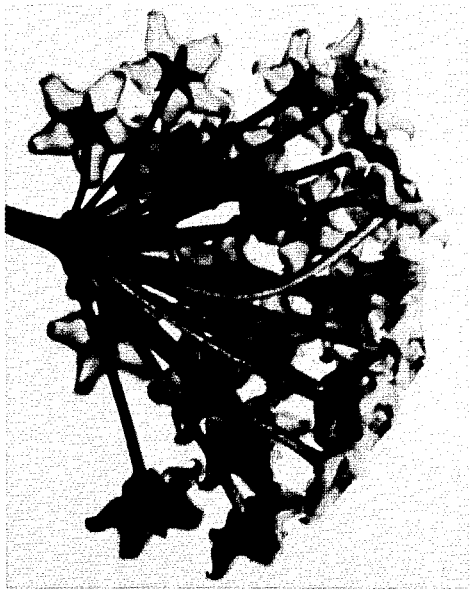
FIG. 4 is another color photograph of the inflorescence seen in FIG. 3.

The following is a detailed description of the new plant variety with colors and hues, unless otherwise clearly indicated by the text, being named in accord with the ISCC–NBS method of designating colors (U.S. Department of Commerce, National Bureau of Standards, Circular 553, issued Nov. 1, 1955), the named colors being interpreted from color notations derived by comparison with the color specimens in the current "Neighboring Hues Edition" of the Munsell Book of Color, published by the Munsell Color Company, Inc., of Baltimore, Maryland.

*Plant description*

Name: *Hoya carnosa* (CV) Rubra.

Origin: A sport on a plant of the *Hoya carnosa* Tricolor variety.

Classification:

(A) *Botanic.*—(Asclepiadaceae) milkweed family.

(B) *Commercial.*—Foliage plant.

Form: Semisucculent, tropical, twining vine type perennial evergreen with some branching.

Stems:

(*A*) *General.*—Caulescent, fleshly, herbaceous.

(*B*) *Texture.*—Moderately pubescent during immaturity and with age becoming glaucous and ultimately covered with thick waxy scale.

(*C*) *Size.*—(1) Diameter: characteristically larger in diameter than those of the *Hoya carnosa* Exotica variety and at maturity during the first year being usually between 2 and 5 mm. (2) Internode: usually between 2 and 100 mm. during first year of vine growth.

(*D*) *Color.*—Characteristically dominated by purple, purplish red, red, reddish brown and/or pink hues prior to becoming glaucous. Commonly occurring colors are moderate purplish red (10 RP 4/8), dark purplish red (7.5 RP 3/6) (10 RP 3/6) (10 RP 3/4), grayish purplish red (10 RP 4/6), dark grayish purple (10 RP 3/2), moderate red (5 R 4/8) (5 R 4/10) (2.5 R 4/8), dark red (5 R 3/4) (2.5 R 3/6), light grayish red (2.5 R 6/4) (7.5 R 6/4), grayish red (2.5 R 4/6) (2.5 R 5/6) (5 R 5/6) (7.5 R 5/6), dark grayish red (2.5 R 3/2), dark pink (2.5 R 6/6), and/or dark grayish reddish brown (7.5 R 2/2) (10 R 2/1).

Leaves:

(*A*) *General.*—Simple, exstipulate.

(*B*) *Arrangement.*—Opposite with an occasional nonrepeating alternate occurrence.

(*C*) *Margins.*—Usually entire.

(*D*) *Venation.*—Pinnate.

(*E*) *Shape.*—(1) General: usually ovate with some oval and lanceolate occurrences. (2) Leaf apices: usually from mucronate to acuminate with some acute tendencies. (3) Leaf bases: usually from rounded to acute.

(*F*) *Petioles.*—(1) General: fleshy. (2) Texture: slightly pubescent and with age becoming glaucous and ultimately covered with thick waxy scale. (3) Size: (a) Diameter—usually between 2 and 3 mm. during first year of maturity. (b) Length—usually between 6 and 20 mm. during first year of maturity. (4) Color: characteristically dominated by purple, purplish red, red, reddish brown, pink and/or yellowish pink hues prior to becoming glaucous. Commonly occurring colors are moderate purplish red (10 RP 4/8), dark purplish red (10 RP 3/6) (7.5 RP 3/4) (10 RP 3/4), grayish purplish red (10 RP 5/6), moderate red (5 R 4/8) (5 R 5/8), dark red (2.5 R 3/4) (5 R 3/4), grayish red (2.5 R 4/4) (2.5 R 4/2) (7.5 R 4/4) (5 R 4/6) (5 R 5/6), light grayish red (5 R 6/4), moderate reddish brown (10 R 3/6), deep pink (2.5 R 6/8) (5 R 6/8), moderate pink (5 R 7/6), moderate yellowish pink (2.5 YR 8/4), and/or dark grayish purple (10 RP 3/2).

(*G*) *Leaf blades.*—(1) General: semisucculent and characteristically variegated in patterns characteristic of the *Hoya carnosa* Exotica variety with the upper epidermal blade part generally having an albino center field or area which is surrounded by a green border area, and with the lower epidermal blade part having a splotched or streaked background field. (2) Texture: (a) Upper epidermis—slightly pubescent during immaturity and with smooth waxy appearing surface during maturity. (b) Lower epidermis—moderately pubescent and heavily glaucous at maturity. (3) Size: (a) Length—usually between 25 and 85 mm. during first year of maturity. (b) Width—characteristically wider than blades of the *Hoya carnosa* Exotica variety and usually between 15 and 50 mm. during first year of maturity. (4) Color: (a) Upper epidermal part— (1) Albino center area: characteristically dominated during immaturity by purplish pink, purplish red, pink, red and/or yellowish pink hues that gradually fade out of the area during maturity. Commonly occurring colors during immaturity are pale purplish pink (7.5 RP 8/4), moderate purplish pink (7.5 RP 7/8), deep purplish pink (7.5 RP 6/10), moderate pink (5 R 8/4) (2.5 R 7/6) (10 RP 7/6), dark pink (2.5 R 6/6) (5 R 6/6), deep pink (10 RP 6/8), strong pink (10 RP 7/8) (2.5 R 7/8), moderate purplish red (10 RP 4/10) (10 RP 5/8) (7.5 RP 5/10), grayish purplish red (10 RP 4/6), moderate red (2.5 R 4/10) (2.5 R 5/8), and/or light-moderate yellowish pink (7.5 R 8/4). Commonly occurring colors after fading out are yellowish white (near 10 YR 9/2) (near 2.5 Y 9/2) (near 7.5 Y 9/2), pale yellow green (10 Y 9/2), pale greenish yellow (7.5 Y 9/4) (10 Y 9/4), light greenish yellow (7.5 Y 9/6) (10 Y 9/6), pale yellow (5 Y 9/4) (2.5 Y 9/4) (near 2.5 Y 9/2) (near 7.5 Y 9/2), light yellow (5 Y 9/6) (2.5 Y 9/6), brilliant yellow (5 Y 9/8), pale orange yellow (near 10 YR 9/2), and/or pale yellowish green (10 Y 9/2). (2) Green border area: characteristically overcast during early immaturity with color which is concentrated in the upper epidermal region of the blade and which endows the border area to the ordinary eye with a blackish and/or brownish appearance that fades out of the area. Commonly occurring colors during early immaturity are purplish black (near 10 RP 2/1), reddish black (near 2.5 R 2/1) (near 5 R 2/1), blackish purple (near 10 RP 2/1) (near 10 RP 2/2), dark grayish purple (near 10 RP 2/1) (near 10 RP 2/2) (near 7.5 RP 2/2), blackish red (near 2.5 R 2/1) (near 5 R 2/1) (near 2.5 R 2/2) (near 5 R 2/2), dark grayish red (near 2.5 R 2/1) (near 5 R 2/1) (near 2.5 R 2/2) (near 5 R 2/2), very dark red (near 2.5 R 2/2) (near 5 R 2/2), dark purplish red (near 10 RP 2/2) (near 7.5 RP 2/2), very dark purplish red (near 10 RP 2/2) (near 7.5 RP 2/2), dark grayish brown (5 YR 2/1), grayish brown (5 YR 3/2) (7.5 YR 3/2), grayish reddish brown (near 2.5 YR 3/2), dark grayish reddish brown (near 2.5 YR 2/2), grayish olive (10 Y 3/2) (5 Y 3/2) (7.5 Y 3/2), dark grayish yellowish brown (10 YR 3/2), and/or moderate olive brown (2.5 Y 3/2). Commonly occurring colors after fading are moderate olive green (7.5 GY 3/4) (7.5 GY 4/4) (7.5 GY 4/6) (2.5 GY 4/4), dark yellowish green (10 GY 3/4) (10 GY 4/4) (10 GY 4/6), strong yellow green (2.5 GY 7/8) (2.5 GY 6/8) (5 GY 7/8) (5 GY 6/8) (7.5 GY 6/8) (7.5 GY 7/10) (7.5 GY 7/8) (7.5 GY 6/10), and/or moderate yellow green (2.5 GY 5/6) (5 GY 5/6) (5 GY 6/6) (7.5 GY 5/6) (7.5 GY 6/4) (7.5 GY 6/6) (5 GY 7/6) (2.5 GY 5/6). (b) Lower epidermal part—(1) Splotches and streaks: commonly moderate yellow green (5 GY 5/4) (5 GY 6/4) (7.5 GY 6/4) (5 GY 6/6) (5 GY 7/4) (2.5 GY 7/6). (2) Background: commonly occurring colors are pale greenish yellow (10 Y 9/4) (7.5 Y 9/4), light greenish yellow (10 Y 9/6), and/or light yellow green (5 GY 9/4) (2.5 GY 9/6).

Inflorescence:

(*A*) *Form.*—Simple umbel with minute 5-merous bracts and usually from 15 to 45 flowers in a cluster.

(*B*) *Peduncles.*—(1) General: hard, fleshy. (2) Texture: slightly pubescent and with age becoming glaucous and ultimately covered with thick waxy scale. (3) Size: (a) Length—usually 20 to 40 mm. at maturity. (b) Diameter—usually between 1 and 4 mm. at maturity. (c) Color—characteristically dominated by purplish red, red and/or reddish brown hues prior to becoming glaucous. Commonly occurring colors are moderate grayish purplish red (7.5 RP 4/6) (10 RP 4/4), moderate purplish red (10 RP 4/10) (10 RP 5/8) (10 RP 4/8), dark purplish red (7.5 RP 3/6) (7.5 RP 4/6) (10 RP 3/4), dark red (5 R 3/4) (2.5 R 3/4), and/or moderate reddish brown (7.5 R 3/4).

(*C*) *Pedicels.*—(1) General: soft, fleshy. (2) Texture: sparcely pubescent. (3) Size: (a) Length—usually 25 to 35 mm. (b) Diameter—usually between 1 and 2 mm. (4) Color—characteristically dominated by purplish red and/or red hues. Commonly occurring colors are dark red (2.5 R 3/6) (5 R 3/6) and/or moderate purplish red (10 RP 5/10) (10 RP 4/8) (7.5 RP 4/8).

(*D*) *Flowers.*—(1) General: complete, perfect, actinomorphic and 5-merous type flower with hypogynous perianth and alternate sepal-petal and petal-corona segment arrangements. (2) Size: usually 15 to 20 mm. in diameter. (3) Calyx: (a) General—5-merous with separate, valvate sepals. (b) Sepal texture—(1) Upper epidermis: smooth glabrous. (2) Lower epidermis: moderately pubescent. (c) Sepal size—proximal to distal end length is usually about 3 mm. (d) Sepal color—characteristically dominated by purplish red, red and/or reddish brown hues. Commonly occurring colors are dark purplish red (10 RP 3/4) (10 RP 3/6), grayish red (2.5 R 4/4), and/or dark red (2.5 R 3/6) (2.5 R 3/4). (4) Corolla: (a) General—5-merous, valvate and rotate with interpetal basal fusion for about 1/2 petal length. (b) Petal texture—(1) Upper epidermis: very dense velvety pubescence. (2) Lower epidermis: glabrous and waxy. (c) Petal size—proximal to distal end length usually about 6–7 mm. (d) Petal color—(1) Upper epidermal side: characteristically dominated by purplish pink and/or pink hues. Commonly occurring colors are dark purplish pink (5 RP 6/8) (7.5 RP 6/6), moderate purplish pink (5 RP 7/6), and/or dark pink (10 RP 6/6). (2) Lower epidermal side: characteristically dominated by a purplish red hue. Commonly occurring colors are moderate purplish red (7.5 RP 4/8) (10 RP 4/10), dark purplish red (7.5 RP 3/6) (5 RP 3/8), and/or grayish purplish red (5 RP 4/6). (5) Corona: (a) General—5 merous, hornlike segments which are adnate to stigma and corolla and crested at their proximal ends. (b) Segment texture—hard, smooth, waxy and glabrous. (c) Segment color—(1) Proximal end: commonly dark grayish purple (7.5 RP 3/2) and/or dark purplish red (7.5 RP 3/6) (7.5 RP 3/4) (5 RP 3/4) and merging with distal end color. (2) Distal end: commonly yellowish white (5 Y 9/1) (10 Y 9/1) (7.5 Y 9/1) and/or pale yellow green (10 Y 9/2) and merging with proximal end color. (6) Androecium: (a) General—5 merous pollinium pairs partially enclosed by expanded translucent parenchymatous translators and attached to stigma through corpuscula located between adjacent segments and with pollinia and translators rising above corpuscula and stigma in converging conical arrangement. (b) Pollinium color—commonly brilliant yellow (near 2.5 Y 8/10) (near 5 Y 8/10) and/or strong yellow (near 2.5 Y 8/10) (near 5 Y 8/10). (7) Gynoecium: (a) General—compound and apocarpous pistil with common stigma. (b) Stigma—(1) General: 5-lobed and waxy. (2) Color: commonly light moderate yellow (2.5 Y 8/7) and/or light brilliant yellow (near 5 Y 9/8). (c) Style—lacking. (d) Ovary—(1) General: two monocarpellate ovularies with axillary placentation of ovules. (2) Color: commonly dark purplish red (10 RP 3/6).

The above description is based on observations of well fertilized plants of less than two years old from initial propagation and which were grown under 85% shaded nursery conditions in the Winter Garden, Fla. area and wherein temperatures range approximately from 60–85 degrees F. during the winter months and from 75 degrees to 95 degrees F. during the summer months.

The following is a general description of a plant of the new variety that was propagated from a stem cutting and which was taken in the month of November about 80–90 days after the cutting was first planted in a nursery at Winter Garden, Fla.

Stem:

(*A*) *Length.*—About 9 inches.

(*B*) *No. of nodes.*—6 plus 2 with embryonic leaves.

(*C*) *Diameter.*—Ranges from about 1½ mm. at tip to about 4 mm. near the rooted cutting.

(*D*) *Internode distance.*—Varies from about 8 mm. to about 54 mm.

(*E*) *Color.*—Dark purplish red (10 RP 3/6), moderate purplish red (10 RP 4/8) and moderate red (2.5 R 4/8).

Leaves:

(*A*) *No. of nonembryonic leaves.*—8 matures plus 4 immature including 2 newly immature (less than 15 days old).

(*B*) *Petioles.*—(1) Diameter—vary from 2–3 mm. at maturity. (2) Length—vary from 10–19 mm. at maturity. (3) Color—dark grayish purple (10 RP 3/2), dark purplish red (10 RP 3/4) and dark red (2.5 R 3/4).

(*C*) *Blades.*—(1) Width—vary from 28–36 mm. at maturity. (2) Length—vary from 48–72 mm. at maturity. (3) Color—(a) Upper epidermal albino area; (1) Immature: moderate red (2.5 R 4/10), moderate pink (10 RP 7/6) and dark pink (5 R 6/6). (2) Mature: yellowish white (near 10 YR 9/2), pale yellow (near 7.5 Y 9/2) and pale yellowish green (10 Y 9/2). (b) Upper epidermal green border area: (1) Newly immature: grayish olive (7.5 Y 3/2) (5 Y 3/2). (2) Mature: moderate olive green (7.5 GY 4/6) (2.5 GY 4/4) and moderate yellow green (5 GY 5/6). (c) Lower epidermal splotched area: (1) Mature: moderate yellow green (5 GY 6/4). (d) Lower epidermal background area: (1) Mature: pale greenish yellow (7.5 Y 9/4) (10 Y 9/4).

The following is a general description of a typical inflorescence that appear on a vine about 18 months old. No. of flowers: 26.

Peduncle:

(*A*) *Size.*—(1) Length: about 28 mm. (2) Diameter: about 2 mm.

(*B*) *Color.*—Dark purplish red (10 RP 3/4) and dark red (2.5 R 3/4).

Pedicels:

(*A*) *Size.*—(1) Length: vary from about 27 mm. to 31 mm. (2) Diameter: about 1½ mm.

(*B*) *Color.*—Dark red (2.5 R 3/6) and moderate purplish red (10 RP 4/8).

Flowers:

(*A*) *Size.*—18–19 mm. in diameter.

(*B*) *Sepal size.*—Proximal to distal end length about 3 mm.

(*C*) *Sepal color.*—Dark purplish red (10 RP 3/4) and dark red (2.5 R 3/4).

(*D*) *Petal color.*—(1) Upper epidermal side: dark purplish pink (7.5 RP 6/6) and dark pin (10 RP 6/6). (2) Lower epidermal side: dark purplish red (7.5 RP 3/6).

(*E*) *Corona segment color.*—(1) Proximal end: dark purplish red (7.5 RP 3/6). (2) Distal end: yellowish white (7.5 Y 9/1).

(*F*) *Pollinium color.*—Brilliant yellow (near 5 Y 8/10).

(*G*) *Stigma color.*—Light brilliant yellow (near 5 Y 9/8).

(*H*) *Ovary color.*—Dark purplish red (10 RP 3/6).

I claim:

1. The new and distinct plant variety of the milkweed family as described and illustrated and which is principally distinguished by a growth habit which combines the following characteristics:

(1) larger diameter stems than those of the *Hoya carnosa* Exotica variety and which in color are dominated by purple, purplish red, red, reddish brown and/or pink hues prior to becoming glaucous;

(2) leaves with petioles that in color are dominated by purple, purplish red, red, reddish brown, pink and/or yellowish pink hues prior to becoming glaucous, and with leaf blades that are somewhat broader than those of the *Hoya carnosa* Exotica variety, that are variegated in patterns characteristic of the *Hoya carnosa* Exotica variety, that have an albino center area which in color is dominated during immaturity by purplish pink, purplish red, red and/or yellowish pink hues, and that have a green border area which is overcast during early immaturity with color endowing the border area to the ordinary eye with a blackish and/or brownish appearance; and (3) an inflorescence that has a peduncle color dominated by purplish red, red and/or reddish brown hues prior to becoming glaucous, a pedicel color dominated by purplish red and/or red hues, a sepal color dominated by purplish red, red and/or reddish brown hues, a petal which in color at its upper epidermal side is dominated by purplish pink and/or pink hues and which in color at its lower epidermal side is dominated by a purplish red hue.

No references cited.

ROBERT E. BAGWILL, Primary Examiner